(12) United States Patent
Miller et al.

(10) Patent No.: US 8,201,323 B2
(45) Date of Patent: Jun. 19, 2012

(54) HYPODERMIC NEEDLE EXTRACTION AND DISPOSAL SYSTEM AND DEVICE

(76) Inventors: Gary E. Miller, Mayer, MN (US); Scott Aaron Miller, Hutchinson, MN (US)

( * ) Notice: Subject to any disclaimer, the term of this patent is extended or adjusted under 35 U.S.C. 154(b) by 0 days.

(21) Appl. No.: 12/470,866

(22) Filed: May 22, 2009

(65) Prior Publication Data
US 2009/0230008 A1 Sep. 17, 2009

Related U.S. Application Data

(63) Continuation of application No. 10/945,197, filed on Sep. 20, 2004, now abandoned.

(60) Provisional application No. 60/503,909, filed on Sep. 18, 2003, provisional application No. 60/506,256, filed on Sep. 26, 2003.

(51) Int. Cl.
*B23P 19/00* (2006.01)
(52) U.S. Cl. ...... 29/801; 29/426.5; 29/426.3; 220/254.9
(58) Field of Classification Search ............... 29/426.3, 29/426.5, 426.6, 801; 206/210, 366; 220/230, 220/253, 254.1, 254.9, 262, 264
See application file for complete search history.

(56) References Cited

U.S. PATENT DOCUMENTS

| | | | | |
|---|---|---|---|---|
| 3,343,709 A * | 9/1967 | Henderson | ............... | 220/259.5 |
| D287,756 S * | 1/1987 | Szablak et al. | ............... | D24/131 |
| 4,809,850 A * | 3/1989 | Laible et al. | ............... | 206/366 |
| 4,842,138 A * | 6/1989 | Sandel et al. | ............... | 206/370 |
| 4,984,385 A * | 1/1991 | DeLand | ............... | 49/280 |
| 4,989,307 A * | 2/1991 | Sharpe et al. | ............... | 29/240 |
| 5,046,613 A * | 9/1991 | Baudry et al. | ............... | 206/366 |
| 5,107,990 A * | 4/1992 | Wicherski et al. | ............... | 206/366 |
| 5,193,561 A * | 3/1993 | Robb et al. | ............... | 134/57 R |
| 5,272,693 A * | 12/1993 | Fujisawa | ............... | 720/739 |
| 5,277,868 A * | 1/1994 | Langford | ............... | 422/21 |
| 5,288,964 A * | 2/1994 | Walker et al. | ............... | 219/68 |
| 5,415,315 A * | 5/1995 | Ramirez | ............... | 220/345.2 |
| 5,482,207 A * | 1/1996 | Nelson et al. | ............... | 232/43.2 |
| 5,741,230 A | 4/1998 | Miller | | |
| 5,791,471 A | 8/1998 | Radmand | | |
| 5,979,275 A * | 11/1999 | Waluda | ............... | 82/58 |

OTHER PUBLICATIONS

Final Office Action, U.S. Appl. No. 10/945,197, mailed Feb. 25, 2009.
Non Final Office Action, U.S. Appl. No. 10/945,197, mailed Aug. 20, 2008.

* cited by examiner

*Primary Examiner* — David Bryant
*Assistant Examiner* — Christopher Koehler
(74) *Attorney, Agent, or Firm* — Cardle Patent Law Chtd

(57) ABSTRACT

A hypodermic needle extraction device for removing a hypodermic needle from a syringe having a syringe body and a luer, the device including at least one guide rod disposed with the device, a carriage assembly having a carriage slidably mounted on the guide rod, and a needle extraction assembly configured to grasp the needle such that the needle is separated from the syringe body as the syringe body and needle are urged apart.

25 Claims, 14 Drawing Sheets

HYPODERMIC NEEDLE EXTRACTION AND DISPOSAL SYSTEM AND DEVICE

CROSS-REFERENCE TO RELATED APPLICATIONS

This application is a continuation application of U.S. utility application entitled, "Hypodermic Needle Extraction And Disposal System And Device," having Ser. No. 10/945,197, filed Sep. 20, 2004 now abandoned, which claims priority to U.S. provisional patent applications entitled "HYPODERMIC NEEDLE EXTRACTION DISPOSAL DEVICE AND SYSTEM," filed on Sep. 18, 2003 having Ser. No. 60/503,909, and "HYPODERMIC NEEDLE EXTRACTION DISPOSAL DEVICE AND SYSTEM," filed on Sep. 26, 2003 having Ser. No. 60/506,256. Each of the aforementioned applications is entirely incorporated herein by reference.

TECHNICAL FIELD

The present disclosure relates generally to methods and devices for use in processing syringes such as those used in the medical industry. More specifically, the present disclosure relates to hypodermic needle extraction devices that render used syringes safe for disposal and/or recycling.

BACKGROUND

The medical industry has experienced an exponential increase in the incidence of accidental needle punctures experienced during the disposal and/or storage of used syringes. Accidental needle punctures pose a potentially deadly and serious problem to medical care providers, as well as to individuals handling used syringes. Accidental "needle sticks" may also be costly to diagnose and/or treat. It is estimated that the expense to identify and treat a medical condition acquired as a result of a "needle stick" is within the range of between two thousand and five hundred thousand dollars ($2,000.00 and $500,000.00).

Medical industry insurers have been desperate to identify ways to eliminate and/or minimize the risk of inadvertent "needle sticks" to medical service providers and/or individuals involved in the handling and disposal of used syringes. In addition, self-insuring medical facilities are especially interested in a cost effective solution to eliminate the growing "needle stick" problem.

Currently, used syringes are collected and/or held in a heavy walled bag known in the industry as a sharp bag or box. Currently, a care giver is required to deposit a used syringe and needle into an appropriate sharp bag or box. A number of disadvantages arise through the use of a sharp bag or box by a care giver. Initially, a care giver is required to exercise extreme caution to not acquire an inadvertent "needle stick" during the placement of a used syringe into a sharp bag. In addition, used needles protruding from a sharp bag pose a serious risk to a care giver as the sharp bag becomes filled to capacity. Persons handling a sharp bag filled with used needles must also be extremely careful to not obtain an accidental "needle stick," especially when emptying the syringes or transporting the sharp bag. Frequently, sharp bags are not automatically sealed, thereby further increasing the potential of inadvertent "needle sticks" to individuals. As well, syringes are typically not sterilized prior to transportation, storage, and/or disposal.

Additional risks are also present with respect to the handling of used syringes outside of a medical facility environment. Home health care, such as that practiced by many individuals having diabetes, may require the disposal of a number of used syringes each day. Additionally, used syringes may be disposed of without destruction, which, in turn, may further expose the public to the danger of improper reuse and/or "needle sticks."

The considerations referenced above are just a few of the major problems associated with the handling and disposal of used syringes. The considerations identified above also show a critical need for a device which safely and effectively renders used syringes harmless and non-reusable, thereby facilitating disposal and/or recycling.

Therefore, there is a need for improved methods and devices for rendering used syringes safe for disposal and/or recycling that address these and other shortcomings of the prior art.

SUMMARY

Briefly described, the present disclosure relates to a hypodermic needle extraction and disposal device for removing a hypodermic needle from a syringe having a syringe body and a luer. The device includes at least one guide rod disposed within said device, a carriage assembly having a carriage slidably mounted on the guide rod, and a needle extraction assembly configured to grasp the needle such that the needle is separated from the syringe body as the syringe body and needle are urged apart.

A further embodiment of the present disclosure relates to a hypodermic needle extraction and disposal device for removing a hypodermic needle from a syringe having a syringe body and a luer. The device includes a housing, a carriage assembly including a carriage disposed within the housing, a motor configured to move the carriage relative to the housing, and a needle extraction assembly configured to grasp the needle such that the needle separated from the syringe body as the needle and the syringe body are urged apart. The device further includes a bin including a bin door, the bin being slidably received within the housing and configured to receive the needle after separation from the syringe body. The bin door is configured to move to a shut position as the bin is removed from the housing and move to an open position as the bin is inserted into the housing.

Other objects, features and advantages of the present disclosure will become apparent upon reading the following specification, taken in conjunction with the accompanying drawings.

BRIEF DESCRIPTION OF THE DRAWINGS

Many aspects of the hypodermic needle extraction and disposal device can be better understood with reference to the following drawings. The components in the drawings are not necessarily to scale, emphasis instead being placed upon clearly illustrating the principles of the present hypodermic needle extraction and disposal device. Moreover, in the drawings, like reference numerals designate corresponding parts throughout the several views.

DETAILED DESCRIPTION

Figure 1:
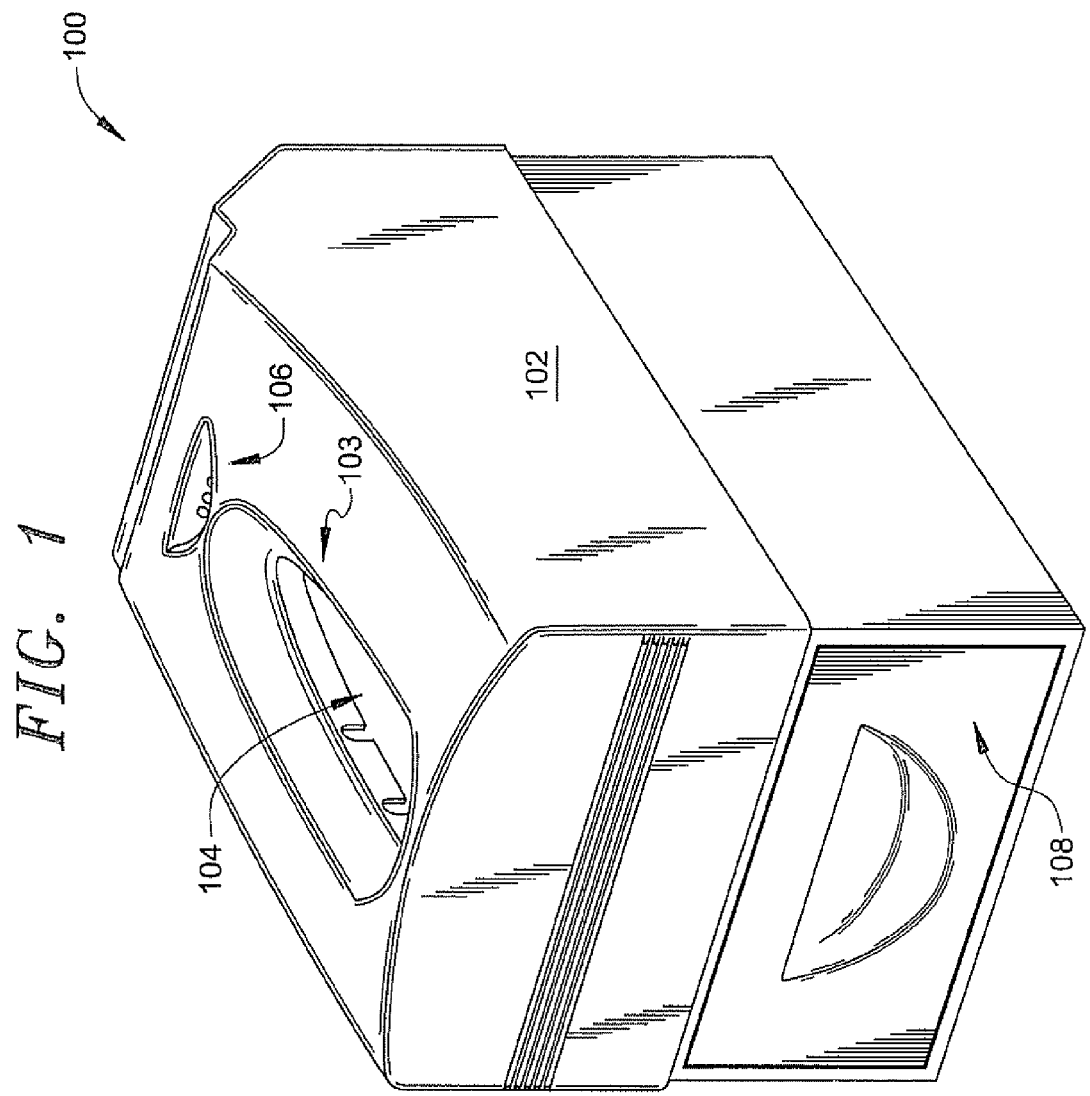
FIG. 1 is a perspective view of an embodiment of an embodiment of internal components of a hypodermic needle extraction and disposal device.

Reference will now be made in detail to the description of the hypodermic needle extraction and disposal device as illustrated in the drawings. While the hypodermic needle extraction and disposal device will be described in connection with these drawings, there is no intent to limit it to the embodiment or embodiments disclosed therein. On the contrary, the intent is to cover all alternatives, modifications, and equivalents included within the spirit and scope of the hypodermic needle extraction device as defined by the appended claims.

In particular, FIG. 1 illustrates an embodiment of a hypodermic needle extraction and disposal device 100 according to the present disclosure. The hypodermic needle extraction and disposal device 100 is used for processing a syringe 12 (FIG. 5) which generally includes a needle 14, a body 16, a luer 18, and a plunger (not shown). The hypodermic needle extraction and disposal device 100 is enclosed within a housing 102, the housing 102 preferably being formed of a lightweight, yet sturdy plastic material.

Figure 9:
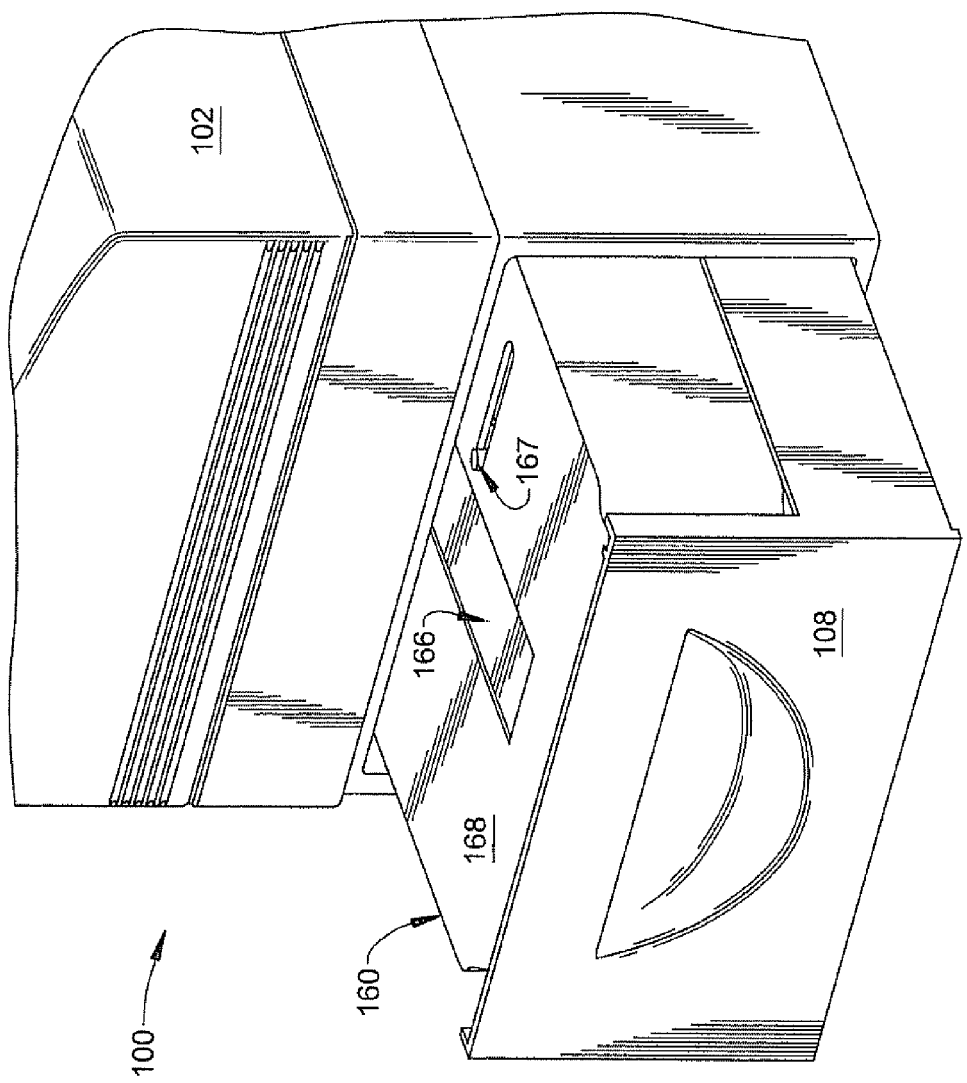
FIG. 9 is a partial perspective view of the hypodermic needle extraction and disposal device shown in FIG. 1.

As shown, the housing 102 includes a number of indicator lamps 106, such as light-emitting diodes (LEDs). Preferably, a ready indicator lamp 106 indicates the availability of the hypodermic needle extraction and disposal device 100 for use in processing a used syringe 12. A bin full indicator lamp 106 indicates the necessity for replacement of either the needle bin and/or the syringe body bin 160 (FIG. 9). The bin full indicator lamp 106 signals when either the needle bin or the syringe body bin 160 have become full following the processing of a plurality of used syringes 12. As well, the housing 102 may also include a power switch and a power input jack (not shown) which may be utilized to supply power to the hypodermic needle extraction and disposal device 100.

As shown, the exterior of the housing 102 also includes a syringe guide cutout 103 which orientates a syringe 12 into position for introduction into the hypodermic needle extraction and disposal device 100. The syringe guide cutout 103 provides a self-contained area for the placement of a syringe 12 prior to processing. The syringe guide cutout 103 is proximate to a syringe receiving door 104 that provides access into the hypodermic needle extraction and disposal device 100. The syringe guide cutout 103 can also be integral to a hopper mechanism (not shown) which is utilized to store a number of used syringes 12 for automatic processing by the hypodermic needle extraction and disposal device 100. The hopper mechanism can function on the same principles as a clip for ammunition, a gravity drop via a channel, a standard shaped hopper, or a conveyor.

Preferably, the syringe receiving door 104 is operated by an electronic control system, as disclosed in U.S. Pat. No. 5,741,230, to Miller, which is incorporated herein by reference in its entirety. The syringe receiving door 104 is opened via a pinion gear 101a engaging a rack 103, thereby permitting a used syringe 12 to enter the hypodermic needle extraction and disposal device 100 for processing.

Figure 2:
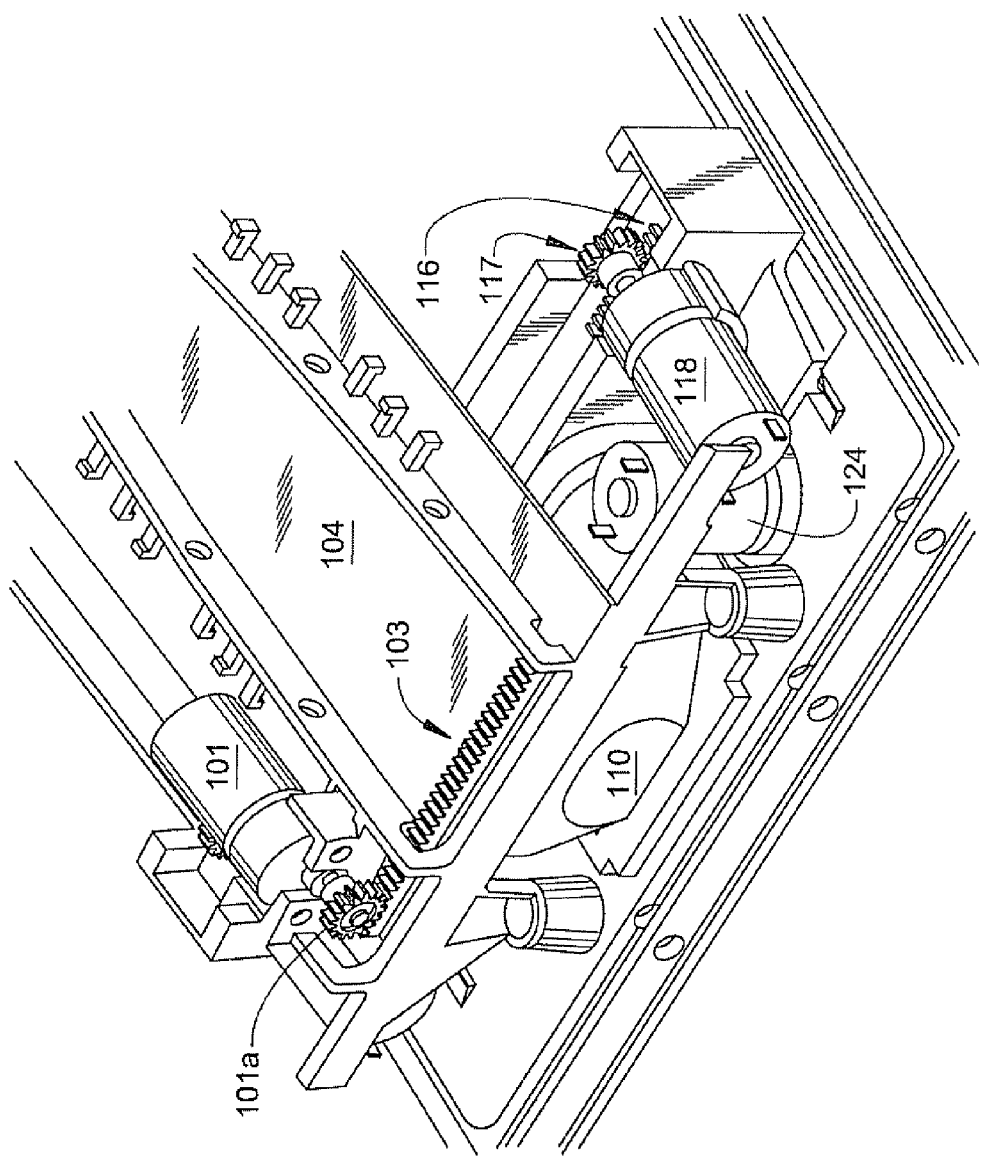
FIG. 2 is a partial perspective view of an embodiment of internal components of the hypodermic needle extraction and disposal device shown in FIG. 1.

As shown in FIG. 2, the syringe receiving door 104 is a platform that is retracted or slid laterally, thereby allowing the syringe to drop vertically into the hypodermic needle extraction and disposal device 100. However, alternate embodiments of the hypodermic needle extraction and disposal device 100 can include a platform having a hinge that permits the platform to rotate downwardly into the interior of the housing 102. A receiving door opto-sensor (not shown) is adjacent the syringe receiving door 104. The receiving door opto-sensor senses the presence of a syringe 12 being placed proximate to the syringe receiving door 104. If no other processing functions are occurring within the hypodermic needle extraction and disposal device 100, the receiving door opto-sensor electrically signals the electronic control system to open the syringe receiving door 104. Preferably, a small motor 101 is used to drive a pinion gear 101a that is operatively connected to a rack 103 located on the syringe door 104. As the syringe receiving door 104 opens the syringe 12 drops into the housing 102 and processing operations are initiated. The syringe receiving door 104 then returns to the closed position.

The receiving door opto-sensor is a proximity device which detects the presence of an object within a certain distance. The receiving door opto-sensor does not physically make contact with a syringe 12. As well, once the receiving door opto-sensor indicates the presence of a syringe 12 proximate the syringe receiving door 104, the electronic control system permits the opening of the syringe receiving door 104 only at such time as the hypodermic needle extraction and disposal device 100 has completed processing of the previous syringe 12 and is ready to initiate further processing procedures.

Figure 3:
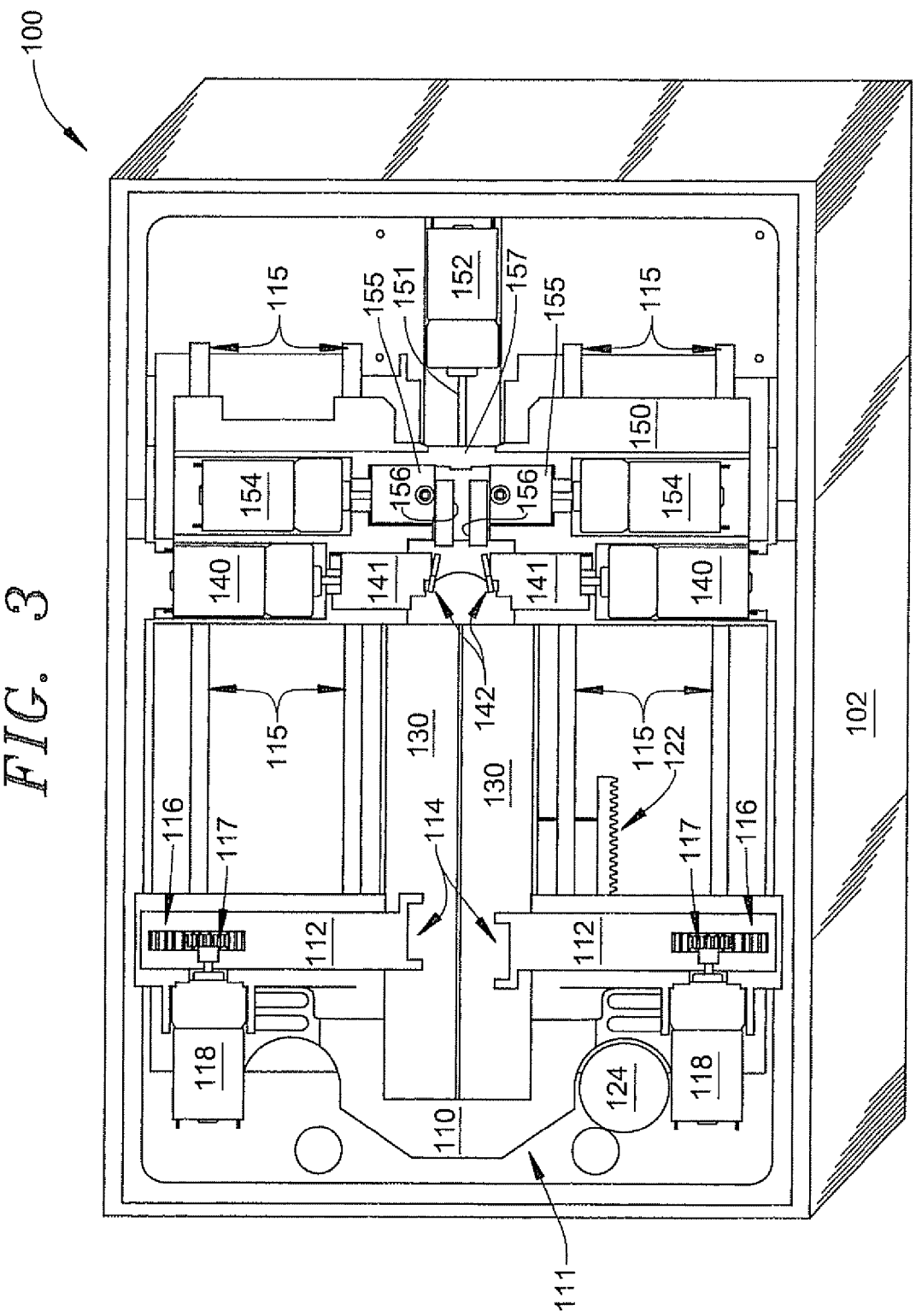
FIG. 3 is a partial perspective view of an embodiment of internal components of the hypodermic needle extraction and disposal device shown in FIG. 1.
Figure 4:
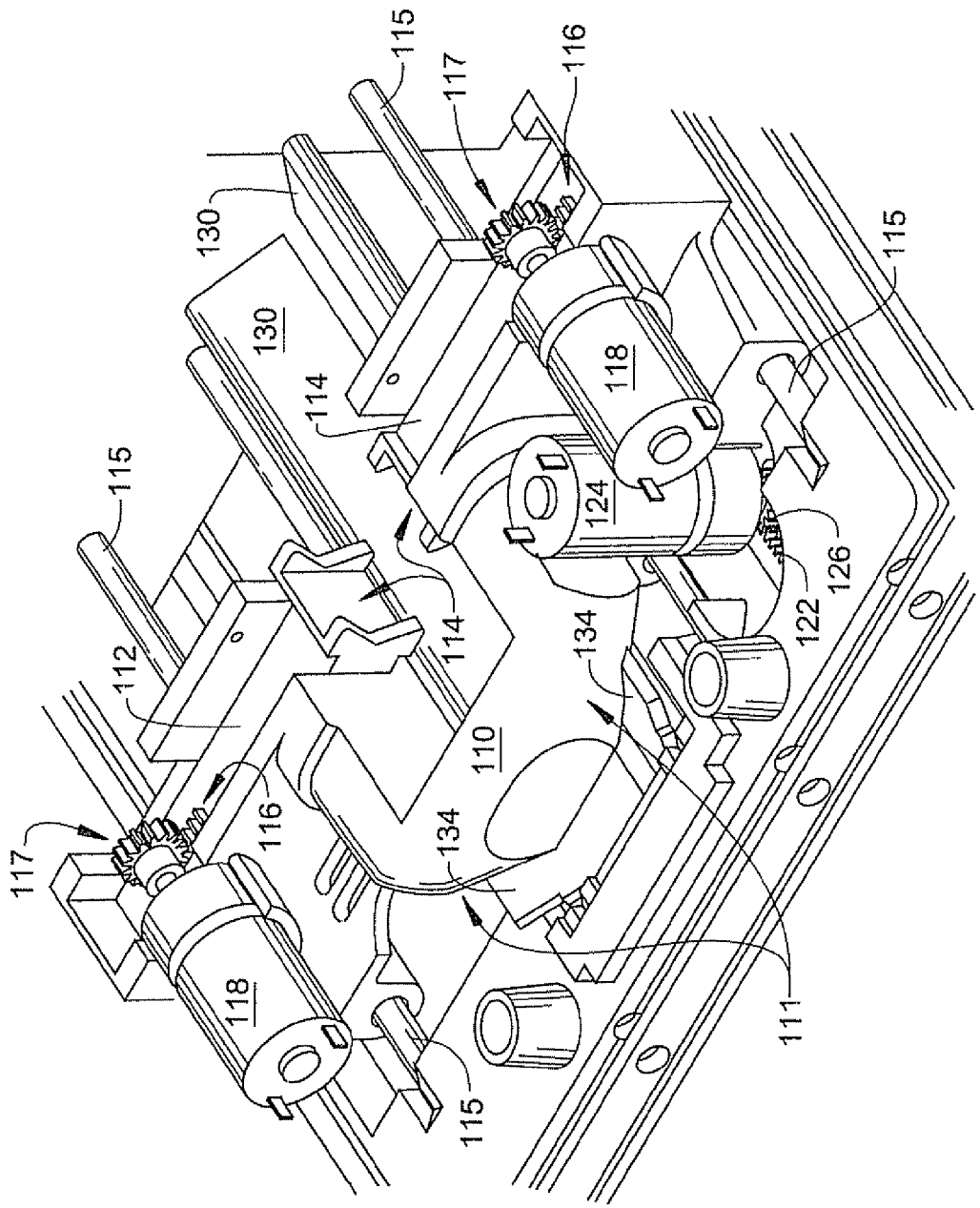
FIG. 4 is a partial perspective view of an embodiment of internal components of the hypodermic needle extraction and disposal device shown in FIG. 1.
Figure 5:
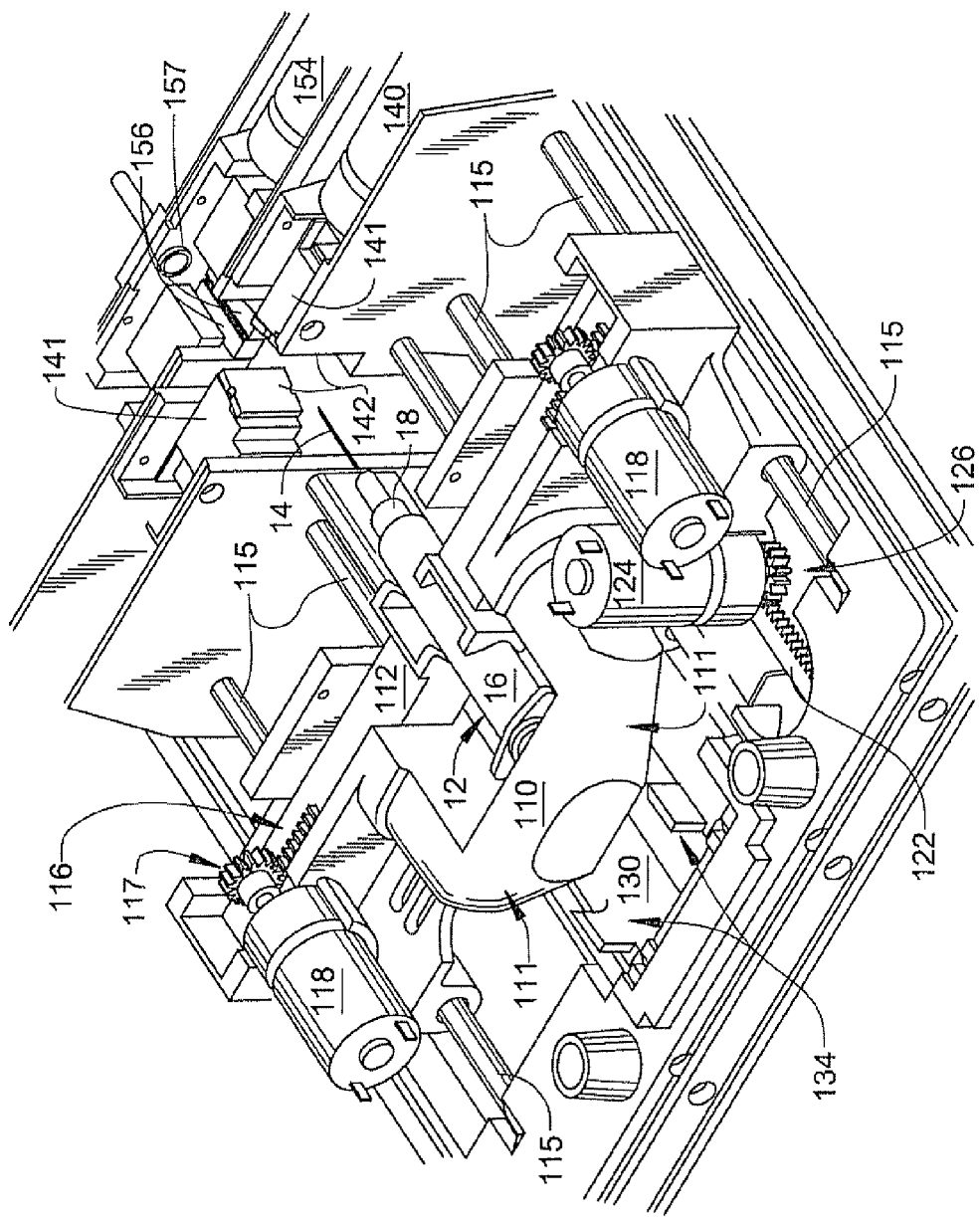
FIG. 5 is a partial perspective view of an embodiment of internal components of the hypodermic needle extraction and disposal device shown in FIG. 1, during operation.

Referring now to FIGS. 3-5, a carriage assembly transports the used syringe 12, as received through the syringe receiving door 104, during processing by the hypodermic needle extraction and disposal device 100. Preferably, the carriage assembly is formed of a carriage 100, a carriage gear rack 122, and a carriage motor 124 having a pinion gear 126.

As shown, the carriage 110 is mounted on a plurality of guide rods 115. Preferably, the guide rods 115 are constructed of stainless steel and allow the carriage 110 to be urged along the guide rods 115 as necessary during processing operations. The carriage 110, when positioned in the at-rest location, is below the syringe receiving door 104 and above a receiving platform formed by the receiving doors 130. Each receiving door 130 is mounted within the housing on a shaft (not shown) such that the receiving doors 130 can freely rotate, as discussed hereafter. When the carriage 110 is in the at-rest position, both receiving doors 130 are horizontally positioned, thereby forming the platform onto which the syringe 12 drops once the syringe receiving door 104 is opened.

Preferably, a carriage opto-sensor (not shown) is positioned adjacent the carriage 110 when the carriage 110 is in the at-rest location under the syringe receiving door 104. The carriage opto-sensor identifies the presence of a syringe 12 on the receiving platform formed by the receiving doors 130 and signals the electronic control system to initiate processing operations.

Preferably, a pair of body clamp plungers 112 is used to both raise the syringe 12 off the receiving platform and to securely clamp the syringe body 16 during processing. The body clamp plungers 112 are oppositely disposed and configured for the centering of the needle 14 in a desired x-y coordinate (FIG. 6), regardless of the varying diameters of the syringe bodies 16. Preferably, each body clamp plunger 112 has a square cross section and is slidably mounted in a square channel on the carriage 110. A pair of barrel clamp motors 118, each barrel clamp motor 118 having pinion gear 117, is used to urge the body clamp plungers 112 inwardly so that they engage the syringe 12. Each pinion gear 117 engages a gear rack 116 formed on the respective body clamp plunger 112. Each gear rack 116 can be either integral to or affixed to the body clamp plunger 112. As well, the square channels may be either affixed to or integral to the carriage 110.

The pair of barrel clamp motors 118 move the barrel clamp heads 114 inwardly for engagement of the syringe 12. The pair of barrel clamp heads 114 are preferably formed in an opposing V-shaped configuration, thereby facilitating the application of an identical clamping pressure to the body 16 of a syringe 12, regardless of the diameter of the body 16. The current or voltage required for clamping of the syringe body 16 by the barrel clamp motors 118 then sensed and/or analyzed by the electronic control system. Upon sensing of a pre-established voltage or current threshold, the electronic control system signals the barrel clamp motors 118 to maintain the barrel clamp plungers 112 in the desired position.

Figure 6:
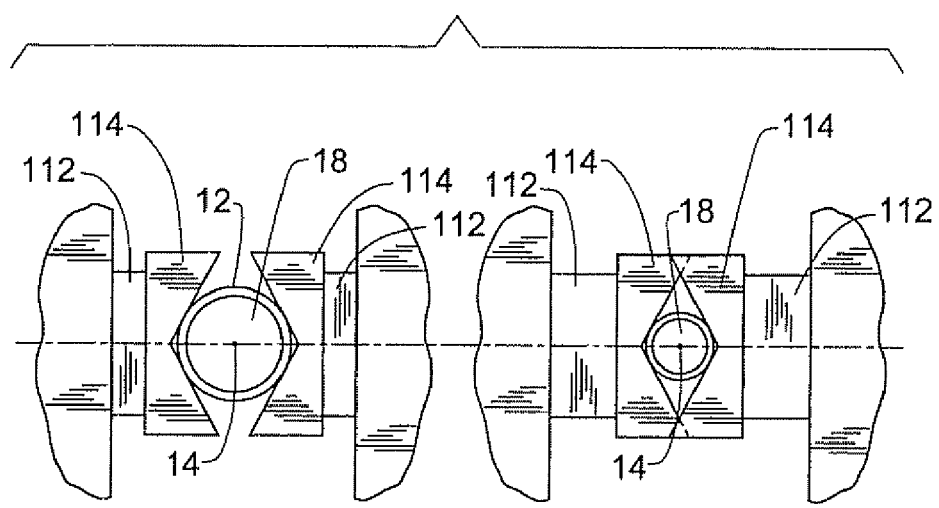
FIG. 6 is a detailed cross sectional end view of the body clamp plungers and syringe, shown in FIG. 5.

The opposing V-shaped clamps of the barrel clamp heads 114 engage the syringe body 16 below the center line to facilitate the elevation and lifting of the syringe 12 for centering in the desired x- and y-coordinate (FIG. 6). The opposing V-shaped barrel clamp heads 114 obtain an identical x- and y-coordinate for the needle 14 regardless of the size of the needle 14 or the diameter dimension for the syringe body 16. The utilization of the square body clamp plungers 112 within the square plunger channels 80 maintains the orientation of the barrel clamp heads 114, thereby maintaining vertical, horizontal, and rotational integrity during operation of the hypodermic needle extraction and disposal device 100. As well, utilization of the square body clamp plungers 112 helps prevent the rotation of the barrel clamp heads 114 out of position.

Preferably, the carriage opto-sensor preferably signals the electronic control system to initiate the grasping of a syringe 12 from the receiving platform. The electronic control system then signals the barrel clamp motors 118 to move the body clamp plungers 112 inwardly so that the barrel clamp heads 114 engage the body 16 of the syringe 12. The engagement between the barrel clamp heads 114 and the syringe body 16 elevates the syringe body 16, positioning the needle 14 in the desired x- and y-coordinate. As the inward positioning of the body clamp plungers 112 continues, increased pressure is exerted upon the body 16. As such, the barrel clamp motors 118 then signal the electronic control system of a desirability of more power. Once a certain power demand threshold has been encountered, the electronic control system signals the barrel clamp motors 118 to maintain the desired position for the remainder of the sterilization and processing procedures of the used syringe 12.

The signal from the carriage stop opto-sensor communicates to the electronic control system that the needle 14 has been positioned as desired, upon which the electronic control system signals the heater assembly to engage the luer 18 of the syringe 12. Preferably, the heater assembly includes a pair of heater motors 140, square plungers 141 positioned within square plunger channels, heater elements 142, and thermalcouples (not shown). The advantages as described for the square plungers and square plunger of the body clamp plungers 112 are equally applicable to the heater assembly described herein.

Preferably, the carriage 110 is moved forwardly and rearwardly along the guide rods 115 by the engagement of the carriage motor 124 which rotates the pinion gear 126 along the carriage gear rack 122. The engagement of the carriage motor 124 occurs through the receipt of signals from the electronic control system. As shown in FIGS. 4 and 5, the electronic control system signals the carriage motor 124 to rotate in a counter-clockwise direction as viewed from above. As such, the carriage 110 is forwardly positioned such that the syringe 12 is proximate to the heater elements 142, which can be ceramic heater heads. It should be noted that if the presence of a luer 18 on the carriage 110 is not identified by the transfer carriage opto-sensor, a signal will be generated to the electronic control system which returns the carriage 110 to the at-rest position.

As seen in FIGS. 4 and 5, as the carriage 110 and syringe 12 are urged forwardly along the guide rails 115, a tab or wing surface 134 on each of the receiving doors 130 slides along a portion of the carriage 110. Preferably, as each wing surface 134 slides along the sloped portion, or bullnose 111, of the carriage 110, each receiving door 130 rotates downwardly such that there is no longer a platform formed beneath the carriage 110. This allows access to the bin 160 positioned thereunder, as is later discussed.

Preferably, the forward motion of the carriage 110 is limited by a carriage stop opto-sensor (not shown) which is positioned adjacent the forward or leading edge of the heater assembly. The carriage stop opto-sensor is preferably adapted to sense and signal the presence of the luer 18 of the syringe 12 in a desired forward location. The carriage stop opto-sensor initiates a signal to the electronic control system upon sensing of the leading edge of the luer 18 of the syringe 12. The carriage stop opto-sensor enables the processing of syringes 12 having varying lengths by terminating the forward motion of all syringes 12 at a standard forward position. At this standard position, the luer 18 is presented in proximity to the heater elements 142 that are located on the square plungers 141. The carriage stop opto-sensor is a proximity device which detects the presence of a non-conductive material within a certain distance, such as a syringe 12.

Figure 7:
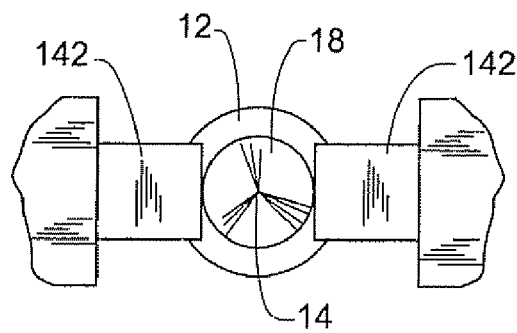
FIG. 7 is a front detailed view of the heater elements and syringe shown in FIG. 5.

Preferably, heater motors 140 engage the square plungers 141 through the utilization of screw shafts and cert nuts. The front surfaces of the square plungers 141 accommodate the heater elements 142. Upon the positioning of the needle 14 in the desired position, the electronic control system signals the heater motors 140 to urge the square plungers 141 inwardly such that the heater elements 142 contact the luer 18 of the syringe 12. Preferably, the electronic control system initiates the application of power to the heater elements 142 when the transfer carriage opto-sensor signals the electronic control system of the presence of a syringe 12 on the receiving platform. As such, the heater elements 142 have already obtained a temperature of approximately 130° Celsius by the time the heater motors 140 receive a signal to position the heater elements 142 into contact with the luer 18. The heater motors 140 urge the heater elements 142 inwardly until such time as an increase in the current/voltage is requested, indicating contact with the luer 18 (FIG. 7). The electronic control system signals the heater motors 142 to terminate the inward positioning of the heater elements 142 while continuing engagement of the heater elements 142 with the luer 18 of the syringe 12. The heater elements 142 then are utilized to soften the luer 18 to facilitate the extraction of the needle 14 from the syringe 12 by the needle extraction assembly. The heater elements 142 can include an angular contact surface which is adapted to flushly engage the luer 18 of the syringe 12 over the entire length of the respective heater element 142.

When the heater elements 142 have acquired a temperature of approximately 130° Celsius, the thermalcouples will signal the electronic control system to terminate/regulate power for the provision of further heat to the heater elements 142. An additional temperature increase to the heater elements 142 is not desired in order to reduce the risk that the heater elements 142 will melt the plastic luer 18 of the syringe 12. Preferably, heater elements 142 soften the luer 18 for extraction of the needle 14, however, they do not fully melt the luer 18. Sufficient power is provided as regulated by the thermalcouples to retain the heater elements 142 at a temperature of approximately 130° Celsius during the softening of the luer 18.

Simultaneous to the engagement of the heater assembly for heating of the luer 18, the electronic control system signals the needle extraction assembly to grasp the needle 14. Preferably, the needle extraction assembly includes a needle extraction platform 150, a platform motor 152, a pair of needle tip clamp motors 154, square plungers 155, square plunger channels, and a pair of needle tip grippers 156, each preferably a carbide gripper.

The needle extraction platform 150 is slidably mounted to a plurality of guide rods 115 which allow for the linear motion of the needle extraction platform 150. Preferably, the needle extraction platform is mounted to the same set of guide rods 115 upon which the carriage 110 is mounted. The forward positioning of the needle extraction platform 150 is preferably limited by the electronic control system via the programming of a distance for forward rotation of the needle extraction shaft 150. It should also be noted that the inward or forward positioning of the needle extraction platform 150 is a known distance which may be pre-programmed as a threshold within the microprocessor of the electronic control system.

The at-rest position for the needle extraction assembly is adjacent the heater assembly. In order to engage the needle 14, the electronic control system signals the needle tip clamp motors 154 to rotate the screw shafts for inward positioning of the square plungers 155 within the square plunger channels. The needle tip grippers 156, having the knurled carbide grippers, are affixed to the square plungers 155. The operations, interactions, and advantages as earlier described for the square plungers 141 and square plunger channels of the heater assembly similarly apply to the needle extraction assembly.

The needle tip clamp motors 152 apply power for the grasping of the needle 14 by the needle tip grippers 156. As the pressure increases between the needle tip grippers 156 and the needle 14, a signal is communicated to the electronic control system for an increased level of voltage or current to be utilized by the needle tip clamp motors 154. The electronic control system signals the needle tip clamp motors 154 to terminate further inward rotation of the screw shafts thereby maintaining the needle 14 securely between the needle tip grippers 156. Simultaneous with the signal from the electronic control system to terminate further pressure upon the needle 14 by the needle tip grippers 156, the electronic control system signals the platform motor 152 to exert a retracting force upon the needle extraction platform 150. The needle extraction motor 152 then moves the needle extraction platform 150 rearwardly away from the luer 18. The needle extraction platform 150 is moved rearwardly via the rotational engagement of the needle extraction shaft 151 and a threaded nut (not shown), that is affixed to, or integral with, the needle extraction platform 150.

As the luer 18 becomes softened following exposure to heat from the heater elements 142, the engagement between the needle 14 and the luer 18 becomes weaker. The luer 18 eventually becomes sufficiently soft to permit the extraction of the needle 14 from the luer 18. During this sequence, the platform motor 152 is exerting a retraction pressure upon the needle extraction platform 150. The platform motor 152 waits for a reduction in the current requirement for extraction of the needle 14, which is indicative of the softening of the luer 18 and the release of the needle 14 from the luer 18. The electronic control system then senses the imminent extraction of the needle 14 from the syringe 12, whereupon the electronic control system increase power to the needle extraction motor 152. As such, the needle tip grippers 156 are retracted, thereby causing separation of the needle 14 from the luer 18. The extracting pressure exerted by the needle extraction motor 152 provides a tugging force upon the needle 14 with respect to the syringe 12. In one embodiment the tugging force upon the needle 14 can be constant. The level of force exerted by the needle extraction motor 152 is sufficient to sense the softening of the luer 18 and the slippage and retraction of the needle 14 from the luer 18.

The extraction of the needle 14 from the syringe 12 and the interaction between the carriage, body clamp plungers, heater assembly, and needle extraction assembly is preferably based upon an event sequence as opposed to a timing sequence. Therefore, the interrelationship is not affected by the diameter dimensions for the syringe body 16 or the needle 14. The electronic control system operates the platform motor 152 and/or the needle tip clamp motors 154 based upon the analysis of the voltage/current requirements for exertion of a desired amount of pressure, whereupon the electronic control system will signal the respective platform motor 152 or needle tip clamp motors 154 to hold an acquired position.

Figure 8:
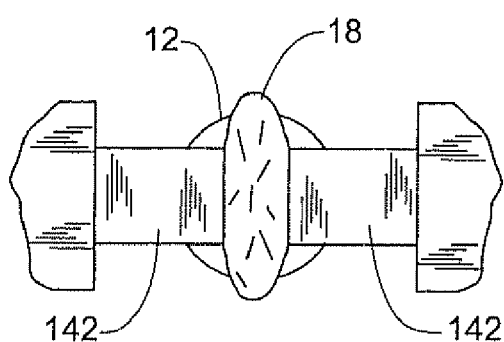
FIG. 8 is a front detailed view of the heater elements engaged to the luer of the syringe.

Simultaneously with the needle 14 separating from the luer 18, the electronic control system signals the heater motors 140 to pinch and collapse the softened luer 18 by the heater elements 142, thereby sealing of the internal cavity of the syringe body 16 (FIG. 8). The heater motors 140 continue to exert compression pressure upon the luer 18 until such time as a threshold is reached, upon which the electronic control system signals the heater motors 140 to retract to an at-rest position. As well, the needle extraction platform 150 is further retracted rearwardly 170 for engagement of the needle 14 to the needle tip contactor assembly (not shown).

Following the sealing of the syringe cavity, the heater elements 142 are retracted to their at-rest position and the electrical control system signals the body clamp motors 118 to retract the body clamp plungers 112 to their start position, thereby permitting the syringe body 16 to drop between the open receiving doors 130 and into the syringe body bin 160 (FIG. 9). The compression and sealing of the luer 18 by the heater elements 142 occurs upon the extraction of the needle 14 from the plastic luer 18 as the base of the needle 14 clears the tip of the plastic luer 18. Compression of the luer 18 upon the separation of the needle 14 from the syringe luer 18 helps prevent contamination or contaminated substance from escaping the syringe 12.

Following the separation of the needle 14 from the luer 18, the needle 14 is sterilized through the establishment of an electrical contact and subsequent heating with the needle tip contactor 157. The needle tip contactor 157 is preferably spring mounted (not shown). The tip contactor 157 includes a conical shaped receiving end which is adapted to engage the tip of a needle 14. The tip contactor 157 is in electrical communication with the needle tip grippers 156.

Preferably, the tip contactor 157 is a spring and formed of a one quarter inch brass diameter shaft having a conical shaped receiving end. A needle 14 engaging the receiving end may thereby be centered for sterilization and processing. Upon engagement of the needle 14 with the tip contactor 157, an electrical connection is established and the electronic control system applies power across the needle 14 such that the needle 14 is used as an element. Preferably, the electronic control system places approximately twelve to twenty volts, corresponding to twelve to fifteen amps, across the needle 14 thereby sterilizing any chemistry or blood which may be present upon the needle 14. The conical shaped receiving end, upon the heating of the needle 14, deforms the point of the needle 14 into a non-reusable condition. The needle tip grippers 156 grasp the needle 14 proximate to the luer 18 in order to maximize the distance between the tip of the needle 14 and the needle tip grippers 156.

The electronic control system then terminates the application of energy across the needle 14 whereupon the needle extraction motor 152 urges the needle extraction platform 150 forwardly for return to the at-rest position. The needle 14 is thereby separated from the conical receiving end. The electronic control system then signals the needle tip clamp motors 154 to retract, separating the needle tip grippers 156 from the needle 14, thereby permitting the needle 14 to drop into the needle bin 130 (FIG. 3). All the elements of the hypodermic needle extraction and disposal device 100 are then positioned for processing of another used syringe 12.

Preferably, the dropped syringe body 16 is received in the syringe body bin 160, as shown in FIG. 9. Similarly, after the needle 14 has been removed and sterilized, the needle 14 is allowed to drop into the needle bin (not shown). Preferably, the needle bin 130 and the syringe body bin 160 are both contained in a single sliding drawer 108. As shown, each bin 160 includes a sliding bin door 166 that functions automatically as the drawer 108 is both pushed into and pulled out of the housing 102.

Figure 10A:
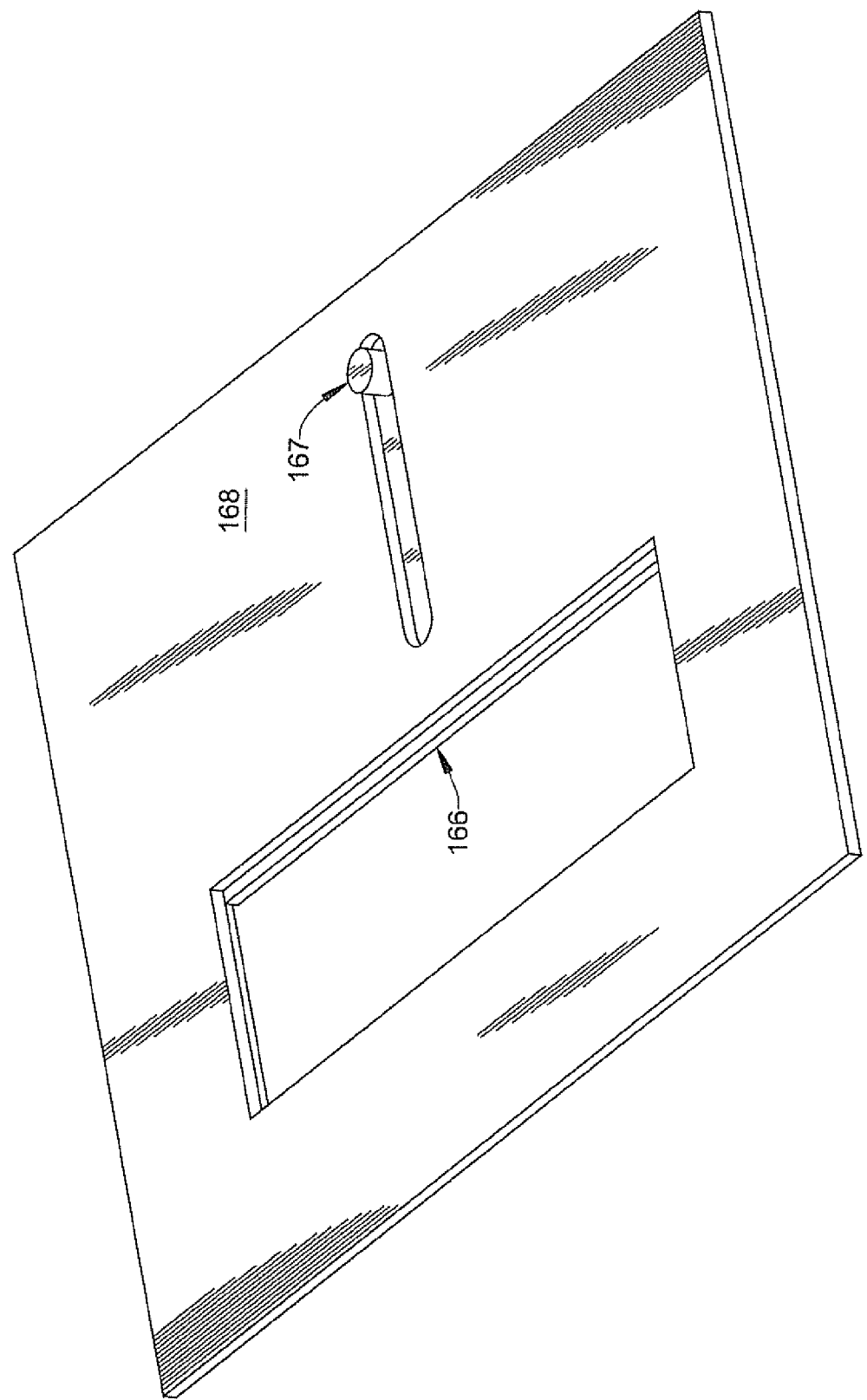
FIGS. 10A and 10B are partial perspective views of a bin cover and bin door, respectively, as shown in FIG. 9.
Figure 10B:
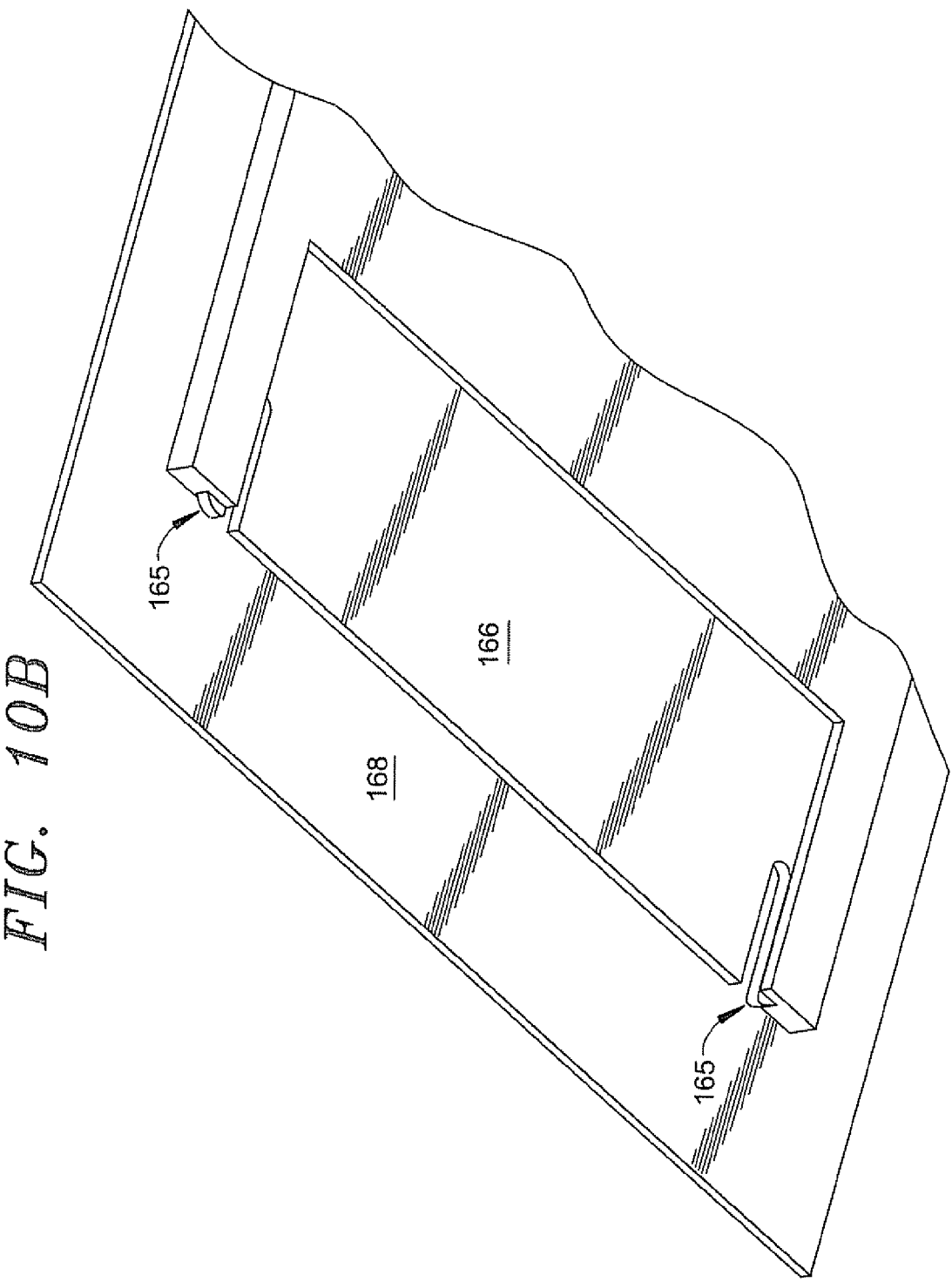

As shown in FIG. 10A, a top view of an exemplary sliding bin door 166 and bin cover 168, an actuator tab 167 extends upwardly from the sliding door 166 and into the bin cover 168. Preferably, the drawer is inserted into the housing 102 with the bin door 166 in an open position. As the drawer 108 is removed from the housing 102, the actuator tab 167 is engaged by angled rails or a slot (not shown) on the underside portion of the housing 102, thereby closing the sliding door 166. As shown in FIG. 10B, a bottom perspective view of the bin cover 168 and sliding door 166, the bin door 166 travels in channels 169 formed on the underside of the bin cover 168. A pair of self-expanding barbs 165 helps lock the sliding door 166 in the closed position after the drawer 108 has been removed from the housing 102. Note, various size drawers and bins may be used depending on the size and/or quantity of the syringes to be processed. As well, bin size selection may depend on whether the unit is used on a countertop, a floor stand, a nurse's cart, is wall mounted, or used by paramedics in the field.

Figure 11:
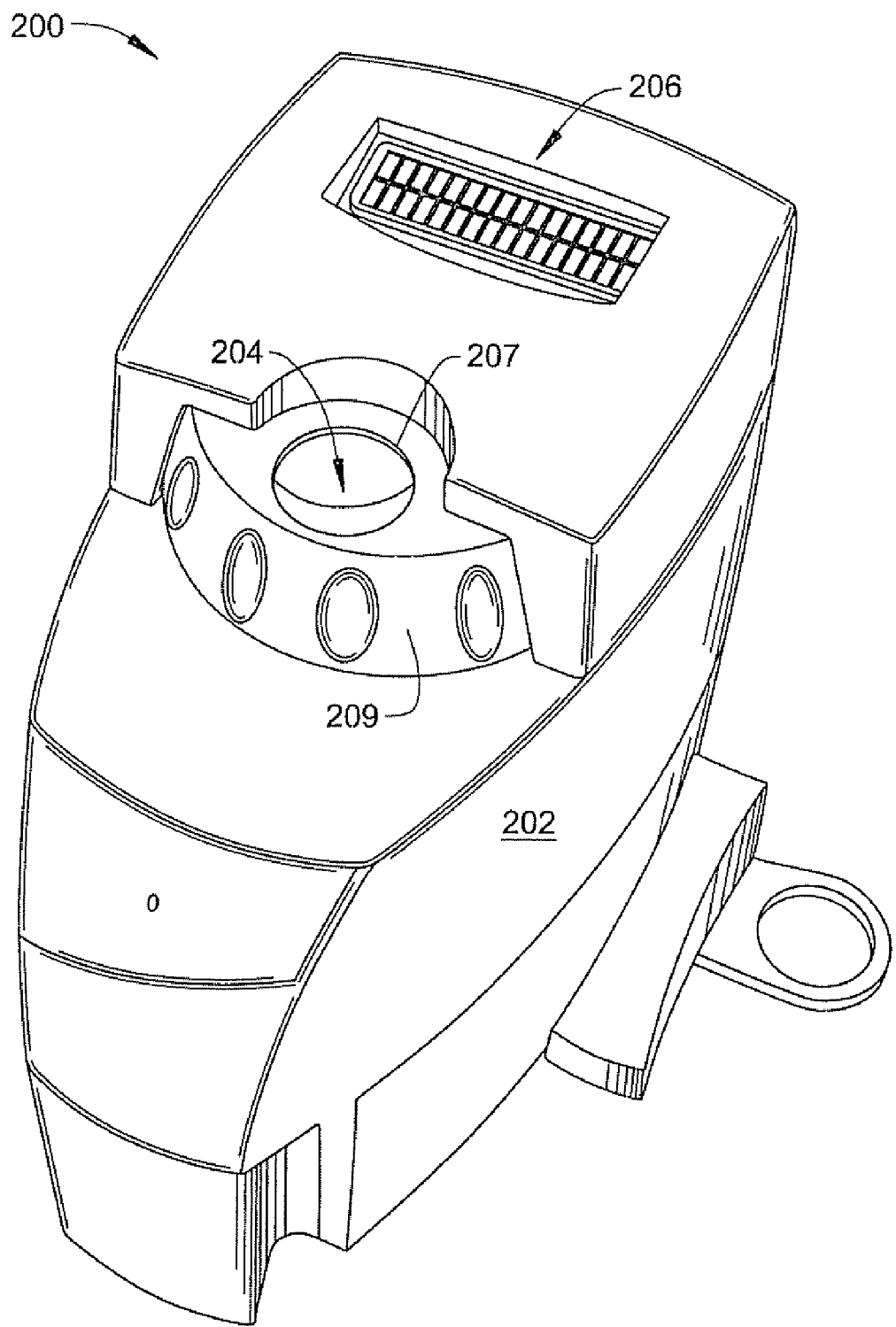
FIG. 11 is a perspective view of an embodiment of a hypodermic needle extraction and disposal device.
Figure 12:
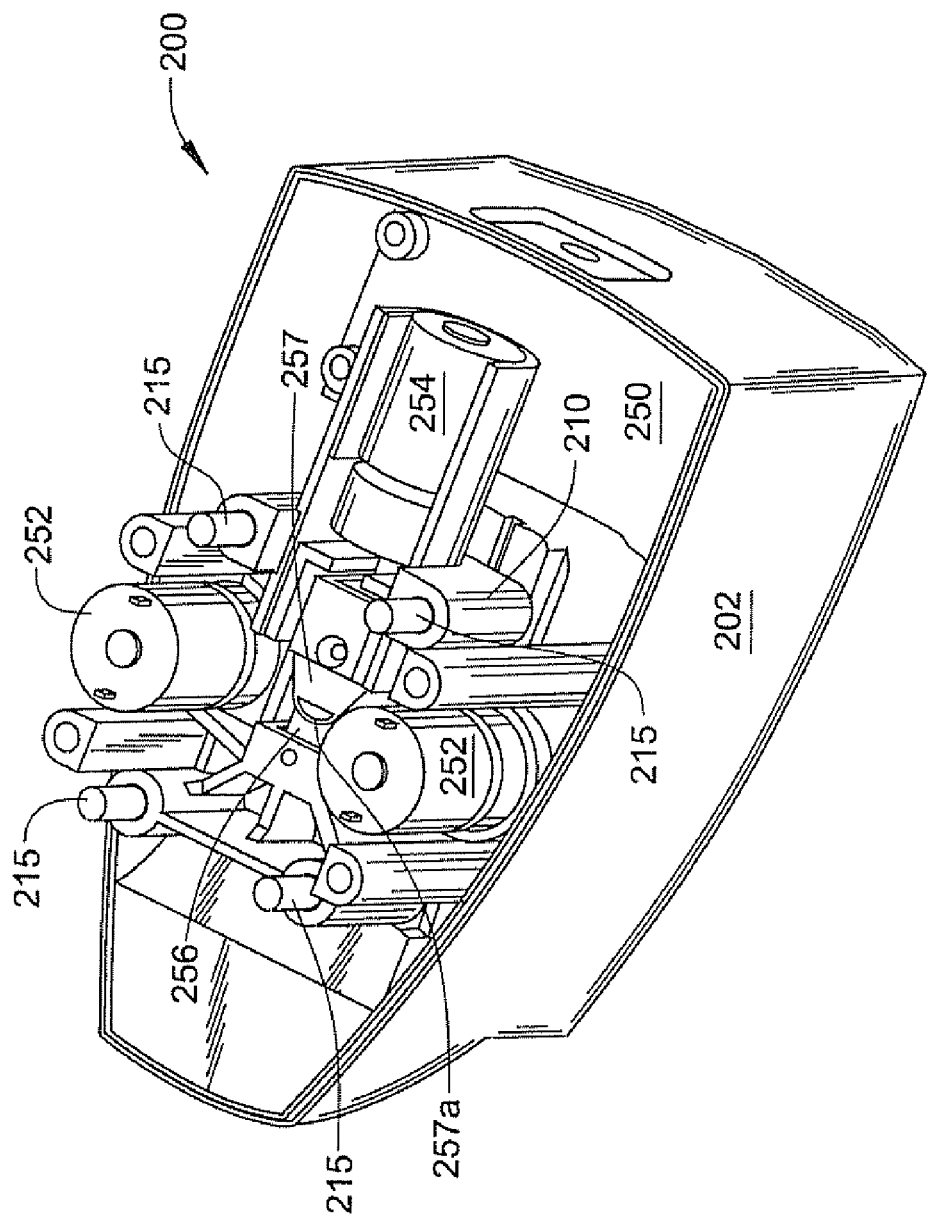
FIG. 12 is a partial perspective view of an embodiment of the internal components of the needle extraction and disposal device shown in FIG. 11.
Figure 13:
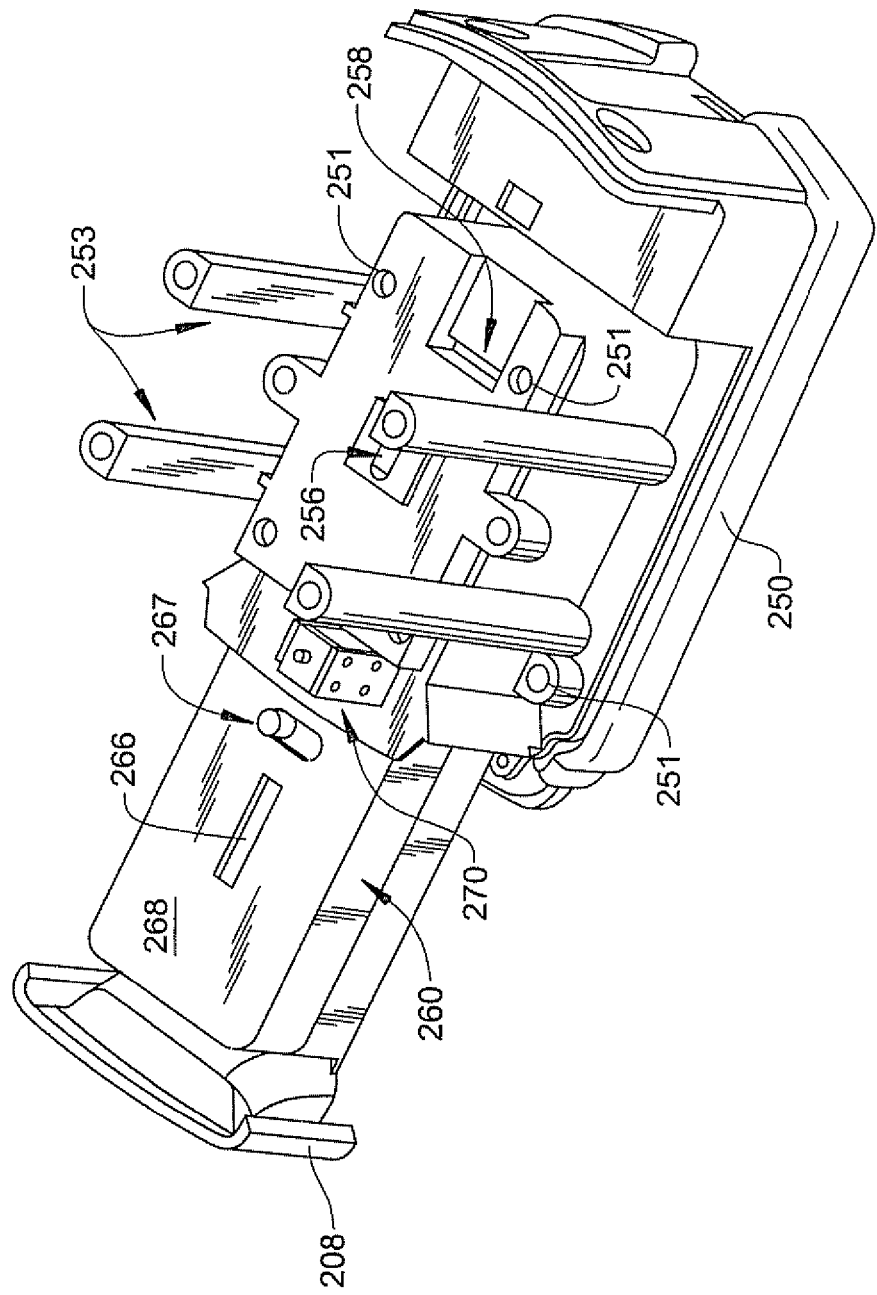
FIG. 13 is a perspective view of a center chassis of the hypodermic needle extraction and disposal device shown in FIG. 12.

An alternate embodiment of a hypodermic needle extraction and disposal device 200 is shown in FIGS. 11-13. As shown, the hypodermic needle extraction and disposal device 200 includes a housing 202 including a needle orifice 204 and a drawer 208 (FIG. 13) slidably received therein. The hypodermic needle extraction and disposal device 200 operates automatically upon insertion of a syringe 12 into the needle orifice 204, either by use of a mechanical switch or by use of opto electronics. Preferably, a wheel 209 is rotatably mounted to the housing 202, the wheel 209 including a plurality of orifice inserts 207 of different sizes. The orifice inserts 207 assist the user in properly positioning the syringe 12 relative to the hypodermic needle extraction and disposal device 200 for removal of the needle 14 therefrom. As well, a liquid crystal display 206 is provided on the housing 202 to provide information to the operator. As previously noted, LEDs can also be used to provide status information to the operator.

Preferably, a movable carriage 210 is slidably mounted within the housing 202 on a plurality of guide rods 215 which are mounted in apertures 251 formed in the center chassis 250 (FIGS. 12 and 13). At the beginning of each processing cycle, the carriage 210 is at the top of its intended range of travel (the range being approximately one inch or less vertically). When the needle 14 of the syringe 12 is inserted into the needle orifice 204, the hypodermic needle extraction and disposal device 200 is activated. Power is provided to the needle tip clamp motor 254 which in turn urges the moveable needle tip gripper 257 toward the opposing stationary needle tip gripper 256, securing the needle 14 therebetween. As the needle tip grippers 256, 257 squeeze the needle 14, the microprocessor senses greater load on the needle tip gripper motor 254. At a predetermined current rise threshold programmed into the microprocessor, the needle tip gripper motor 254 is turned off, leaving the needle 14 secured between the needle tip grippers 256, 257.

After the needle 14 is held firmly by the needle tip grippers 256, 257, the carriage motors are activated, thereby urging the carriage 210 downwardly away from the syringe body 16. The motion of the carriage 210 relative to the syringe body 16 separates the needle 14 from the luer 18. At a predetermined distance (preferably less than one inch), power is secured to the carriage motors 252 as the needle 14 is now free of the luer 18. Preferably, a heater element (not shown) is located adjacent the needle orifice 204 such that when the needle is inserted therein, the luer 18 of the syringe 12 is adjacent the heater element. The heater element softens the luer 18 thereby facilitating removal of the needle from the syringe 12.

The carriage motor 254 is turned on and reversed to separate the moveable needle tip gripper 257 from the stationary needle trip gripper 256, thereby allowing the needle 14 to drop into the needle collection bin 268 (FIG. 13). As a precaution to prevent needles 14 from sticking to one of the needle tip grippers 256, 257, a small loop 257a is attached to the top of the moveable needle tip gripper 257. When the needle 14 is first inserted into the hypodermic needle extraction and disposal device 200, it passes through the loop 257a. As the needle tip grippers 256, 257 are opened, the needle 14 is forced off the face of the stationary needle tip gripper 256 as the needle 14 comes in contact with the edge of the retreating loop 257a. After the needle 14 has been dropped into the needle bin 268, the carriage motors 252 are turned on in reverse and the carriage 210 moves along the guide rods 215 back to the upper position. As soon as the needle 14 has been removed from the luer 18, the user can remove the now needleless syringe body 16 from the needle orifice 204 and place the syringe body 16 in the appropriate waste container.

As best shown in FIG. 13, the drawer 208 and associated needle bin 260 are slidably received in a center chassis 250. Similar to the previously discussed embodiment, the needle bin 260 preferably includes a bin cover 268 with an aperture formed therein and a bin door 266 having an actuator tab 267 extending upwardly therefrom. As the drawer 208 is slid into and out of the center chassis 250, a slot (not shown) formed in the center chassis 250 causes the bin door to be automatically moved to an open and a closed position, respectively. As well, a magnet is embedded in the actuator tab 267 that interacts with a reed switch 258 positioned on the center chassis 250. The reed switch 258 is configured to detect the location of the magnet, and subsequently the actuator tab 257. As such, the reed switch 258 can determine if the bin door 266 has moved to the open position as the drawer 208 is inserted into the center chassis 250. With the bin door 266 in the open position, the aperture in the bin cover 268 is aligned with the needle aperture 256 formed in the center chassis. As such, processed needles 14 can drop into the needle bin 260. If the bin door 266 remains in the closed position for some reason, the reed switch 258 provides a signal to the control system that prevents the operation of the hypodermic needle extraction and disposal device 200.

Preferably, a solenoid 270 is provided that is configured to lock the needle bin 260 in place during operation of the hypodermic needle extraction and disposal device 200 by inserting an actuator (not shown) into a recess (not shown) formed in either the bin 260 or the drawer 208. The solenoid 270 briefly retracts the actuator and allows the drawer 208 to be removed once the needle bin 260 is full. Operation of the solenoid 270 is automatic and based on a count of how many needles 14 have been processed. Preferably, the spring (not shown) positioned within the center chassis 250 forces the drawer 208 out of the center chassis 250 when the solenoid 270 momentarily lifts an actuator (not shown) which normally engages a recess in the drawer 208, thereby holding the drawer 208 in position.

The hypodermic needle extraction and disposal device 200 operates while plugged into a standard 110 V supply, or operates off a battery pack. Preferably, the batteries allow at least 80 to 100 cycles before needing to be recharged. The recharging system is built into the device. No external charging system is necessary. Solar cells may also be mounted on the device to provide operating power and/or recharge the battery pack.

Figure 14:
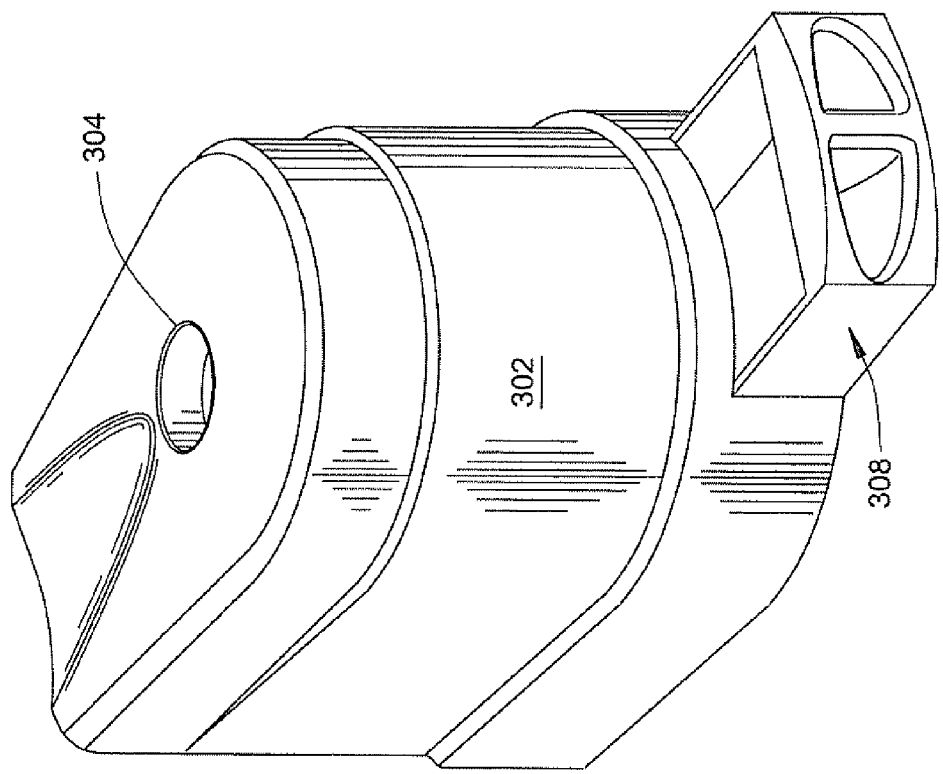
FIG. 14 is a perspective view of an embodiment of a hypodermic needle extraction and disposal device.
Figure 15:
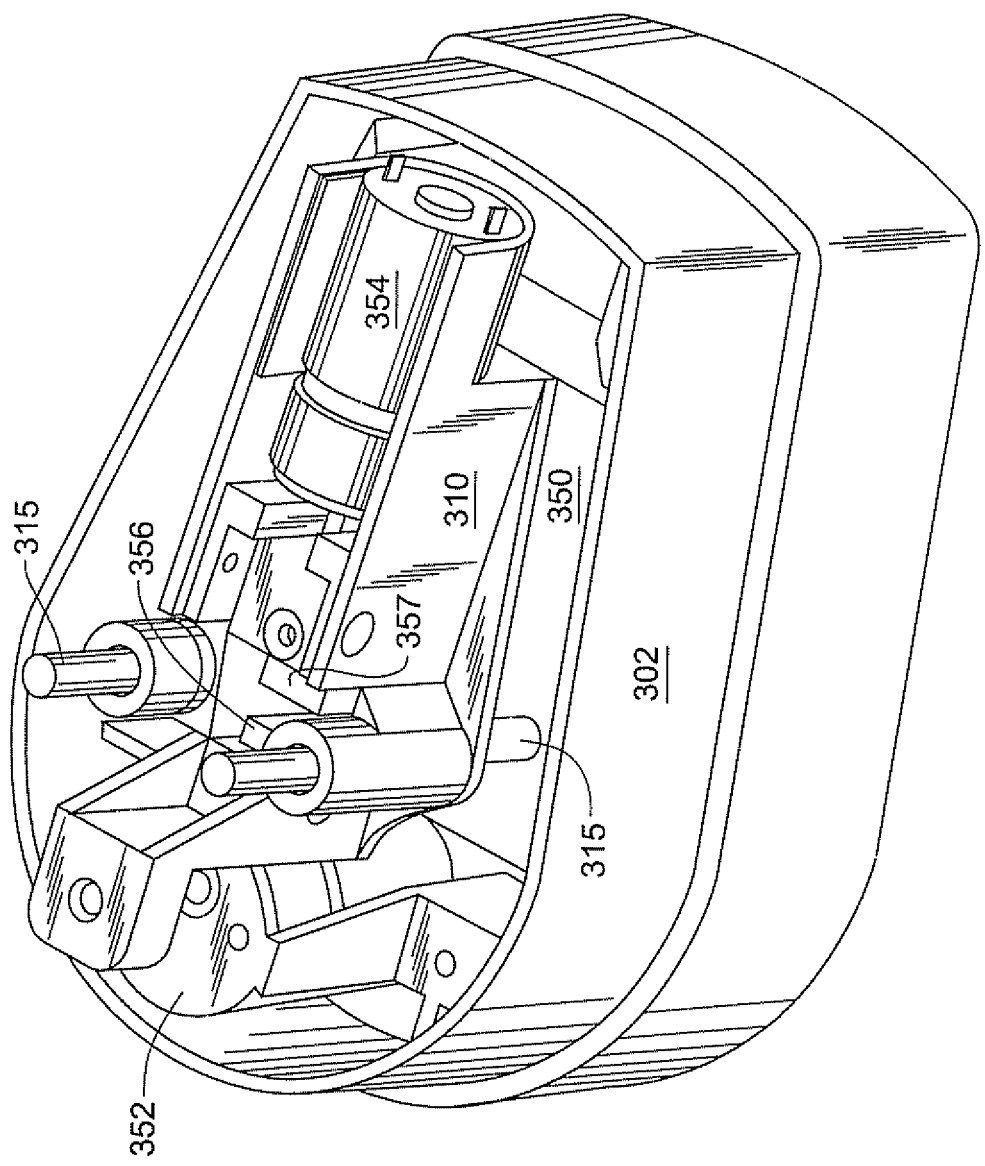
FIG. 15 is a partial perspective view of an embodiment of the internal components of the hypodermic needle extraction and disposal device shown in FIG. 14.

An alternate embodiment of a hypodermic needle extraction and disposal device 300 is shown in FIGS. 14 and 15. As shown, the hypodermic needle extraction and disposal device 300 includes a housing 302 including a needle orifice 304 and a drawer 308 slidably received therein. The hypodermic needle extraction and disposal device 200 operates automatically upon insertion of a syringe 12 into the needle orifice 304, either by use of a mechanical switch or by use of opto electronics.

Preferably, the hypodermic needle extraction and disposal device 300 operates automatically upon insertion of a syringe 12 into the needle orifice, either by use of a mechanical switch or opto electronics. Similar to various other embodiments, the hypodermic needle extraction and disposal device 300 includes a movable carriage 310 slidably mounted therein. As shown, the carriage is mounted on a pair of guide rods 315. As best seen in FIG. 15, at the beginning of each processing cycle, the carriage 310 is at the top of its intended range of travel (the range being approximately one inch or less vertically). When the needle 14 of the syringe 12 is inserted into the needle orifice 304, the hypodermic needle extraction and disposal device 300 is activated. Power is provided to a needle tip clamp motor 354, which in turn urges the moveable needle tip gripper 357 toward the opposing stationary needle tip gripper 356, securing the needle 14 therebetween. As the needle tip grippers 356, 357 squeeze the needle 14, a microprocessor senses greater load on the needle tip gripper motor 354. At a predetermined current rise threshold programmed into the microprocessor, the needle tip gripper motor 354 is turned off, leaving the needle 14 secured between the needle tip grippers 356, 357.

After the needle 14 is held firmly by the needle tip grippers 256, 257, carriage motors 352 are activated, thereby urging the carriage 310 downwardly away from the syringe body 16. The motion of the carriage 310 relative to the syringe body 16 separates the needle 14 from the luer 18. At a predetermined distance (preferably less than one inch), power is secured to the carriage motors 352 as the needle 14 is now free of the luer 18.

The carriage motor 254 is turned on and reversed to separate the moveable needle tip gripper 357 from the stationary needle trip gripper 356, thereby allowing the needle 14 to drop into the drawer 308. Note, a needle bin similar to those previously discussed can be placed in the drawer 308 for the collection of needles 14.

Embodiments are envisioned where the hypodermic needle extraction and disposal device 100 further includes a sterilization module (not shown). For example, after the needle 14 has been extracted from the luer 18, rather than being dropped directly into the syringe bin, the syringe body 16 can be dropped onto a sliding platform and flooded with UV light. After a sufficient period of time has elapsed for the UV light to destroy bacteria, etc., the UV lamp is turned off. Once the UV light is turned off, the platform retracts to one side and the syringe body 16 is allowed to drop into the syringe collection bin. The sliding platform then returns to its home position.

Other embodiments may include a syringe destruction device (not shown) to reduce the syringe bodies 16 to smaller pieces, therefore requiring less storage space in the syringe bin. For example, a syringe destruction device may include a moveable platform on which the syringe is positioned, and then pushed into a grinding or cutting area for reduction. The reduced pieces are then deposited into the syringe collection bin, thereby reducing the volume of storage space required per syringe.

Note, the sterilization unit and syringe destruction device can be either integral parts of the disposal device 100 or can operate independently as stand-alone systems. Preferably, hypodermic needle extraction and disposal device 100 microprocessor has firmware installed to allow for field upgrades of the hypodermic needle extraction and disposal device 100 with the syringe destruction device in the sterilization unit. As such, the microprocessor can determine if one or both of these devices are being used in conjunction with the disposal unit, and will vary all of the operation timing functions accordingly. When the syringe destruction device and sterilization unit are used independently as stand alone systems, they will have their own microprocessor controller and related firmware and hardware.

Embodiments of the hypodermic needle extraction and disposal device 100 are envisioned that have the ability to distinguish between standard syringe/needle combinations and "engineered sharps" (safety syringes—retractable or sheathed). By use of the optic systems incorporated in the hypodermic needle extraction and disposal device 100, the system can determine the type of syringe to be processed. If the syringe is determined to be an engineered sharp, the processing is varied to eliminate the needle extraction portion of the process and the engineered sharp is deposited into the syringe bin. As an alternative to placing or depositing the safety syringe into the normal syringe collection bin, the hypodermic needle extraction and disposal device 100 can be configured to allow for depositing the safety syringes into their own separate syringe collection bin. In this configuration, the disposal device can distinguish between empty syringe barrels with no metal and safety syringes with needles attached.

Various embodiments of the hypodermic needle extraction and disposal device 100 have the ability to communicate through wired and/or wireless LANs (local area networks). As such, hypodermic needle extraction and disposal device 100 can be poled from a central station as to each disposal unit's activity. As well, each hypodermic needle extraction and disposal device 100 can be operated remotely and diagnostics routines can be run to determine if the hypodermic needle extraction and disposal device 100 is functioning properly. A central control system (preferably Windows® based) would allow personnel to communicate with a number of hypodermic needle extraction and disposal device 100 in a system to view activity, status, etc. This allows for management of several hypodermic needle extraction and disposal device 100 on one system.

Embodiments are also envisioned wherein syringe processing events may be time stamped, processed syringe sizes can be determined using look-up tables, the total number of syringes processed in a given amount of time is recorded, and "instructions sets" regarding timing, motor current settings, etc., may be changed via the network connections, depending upon the type syringe being processed.

Although preferred embodiments of the hypodermic needle extraction and disposal device have been disclosed in detail herein, it will be obvious to those skilled in the art that variations and modifications of the disclosed embodiments can be made without departing from the spirit and scope of the hypodermic needle extraction and disposal device as set forth in the following claims.

What is claimed is:

1. A syringe disposal apparatus, comprising:
a housing;
a needle extraction assembly disposed within the housing and operative to separate a needle entirely from a syringe body by urging the needle and the syringe body apart from one another by linear motion of the needle extraction assembly;
a drawer slidably receivable within the housing and operative to receive the needle therein, the needle being separated from the syringe body; and
a bin door disposed about the drawer and adapted to move from an open position to a closed locked position automatically by engagement generally with the housing as the drawer is removed from the housing, the bin door locked permanently in the closed locked position.

2. The apparatus of claim 1, further comprising:
an actuator tab extending from the bin door operable to position the bin door between at least the open position and the closed locked position by motions thereof, the actuator tab movable generally at an angle to the direction of motion of the drawer as the drawer is removed from the housing.

3. The apparatus of claim 2, further comprising:
a slot disposed about the housing and angled with respect to the direction of motion of the drawer, the slot operative to slidably receive the actuator tab to cause motions of the actuator tab effective to position the bin door between at least the open position and the closed locked position as the drawer is removed from the housing.

4. The apparatus of claim 1, further comprising a pair of parallel guide rods disposed within said housing; and
a carriage assembly slidably mounted on the guide rods.

5. The apparatus of claim 1, said carriage assembly further comprising:
a pair of opposed body clamp plungers operative to grasp the syringe body; and
a pair of body clamp motors, each of the body clamp motors operative to move one of said body clamp plungers such that the body clamp plungers grasp the syringe body.

6. The apparatus of claim 4, the needle extraction assembly further comprising:
a platform slidably mounted to the guide rods;
a needle extraction platform motor operative to urge the platform along the guide rods;
a pair of needle tip clamp motors mounted to said platform, each of the needle tip clamp motors including a needle tip gripper; and wherein the needle tip grippers are operative to grip the needle.

7. The apparatus of claim 4, wherein the needle extraction assembly is mounted to the carriage.

8. The apparatus of claim 7, wherein the needle extraction assembly further comprises a stationary needle tip gripper, a movable needle tip gripper, and a needle tip gripper motor operative to urge the movably need tip gripper toward the stationary needle tip gripper, thereby gripping the needle.

9. The apparatus of claim 1, wherein the bin door is locked permanently in the closed locked position as the drawer is removed from the housing by a locking mechanism mounted inaccessibly inside the drawer.

10. The apparatus of claim 9, wherein the locking mechanism comprises a self-expanding barb.

11. The apparatus of claim 10, wherein the self-expanding barb is carried by the bin door.

12. The apparatus of claim 1, wherein the bin door is adapted to move into the open position from an initial position intermediate of the open position and the closed locked position automatically by engagement generally with the housing as the drawer is slideably received within the housing.

13. The apparatus of claim 1, wherein the slidable reception of the drawer within the housing is initiated with the bin door in the open position.

14. The apparatus of claim 1, wherein the needle is sterilized within the housing following separation from the syringe body.

15. The apparatus of claim 14, wherein the syringe body is placed into the drawer.

16. The apparatus of claim 1, wherein the syringe body is sealed following extraction of the needle.

17. The apparatus of claim 1, wherein the drawer is divided into a bin for the placement therein of the syringe body and a bin for the placement therein of the needle.

18. The apparatus of claim 1, wherein the drawer is in locked engagement with the housing when received within the housing, the drawer is released from locked engagement with the housing based upon a count of the needles processed.

19. A syringe disposal apparatus, comprising:
a housing;
a needle extraction assembly disposed within the housing and operative to separate a needle entirely from a syringe body by urging the needle and the syringe body linearly apart from one another;
a drawer slidably receivable within the housing to be held in locked engagement therein, the drawer operative to receive the needle, the needle being separated from the syringe body, the drawer adapted to release from locked engagement based upon a count of the needles received within the drawer; and a bin door disposed about the drawer, the bin door is adapted to move into an open position from an initial position intermediate of the open position and a closed locked position automatically by engagement generally with the housing as the drawer is slideably received within the housing the bin door is adapted to move from the open position to the closed locked position automatically by engagement generally with the housing as the drawer is removed from the housing, with the bin door locked permanently in the closed locked position.

20. The apparatus of claim 19 further comprising:

an actuator tab extending from the bin door operable to position the bin door by motions thereof.

21. A drawer for the disposal of hypodermic needles, comprising:

a drawer slidably receivable within a housing and operative to receive a needle therein, the needle being entirely separated from a syringe body by linear motions of a needle extraction assembly disposed within the housing that urge the needle and the syringe body apart; and a bin door disposed about the drawer, the bin door is adapted to move into an open position from an initial position intermediate of the open position and a closed locked position automatically by engagement generally with the housing as the drawer is slideably received within the housing, the bin door is adapted to move from the open position to the closed locked position automatically by engagement generally with the housing as the drawer is removed from the housing, the bin door locked permanently in the closed locked position.

22. The apparatus of claim 21, wherein the bin door is locked permanently in the closed locked position by a locking mechanism mounted inaccessibly inside the drawer.

23. The apparatus of claim 22, further comprising: a self-expanding barb disposed inside the drawer to lock the bin door permanently in the closed locked position as the drawer is removed from the housing.

24. The apparatus of claim 23, wherein the self-expanding barb is carried by the bin door.

25. The apparatus of claim 21, further comprising: an actuator tab extending from the bin door operable to position the bin door by motions thereof.

* * * * *